US012629205B2

(12) United States Patent
Miri et al.

(10) Patent No.: US 12,629,205 B2
(45) Date of Patent: May 19, 2026

(54) MICROWAVE SEALER DEVICE AND GENERATOR

(71) Applicant: Medtronic Advanced Energy LLC, Minneapolis, MN (US)

(72) Inventors: Mohammad Miri, Longmont, CO (US); Prakash Manley, Arvada, CO (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 647 days.

(21) Appl. No.: 17/249,103

(22) Filed: Feb. 19, 2021

(65) Prior Publication Data

US 2022/0265347 A1 Aug. 25, 2022

(51) Int. Cl.
*A61B 18/18* (2006.01)
*A61B 18/00* (2006.01)

(52) U.S. Cl.
CPC .. *A61B 18/1815* (2013.01); *A61B 2018/0063* (2013.01); *A61B 2018/183* (2013.01); *A61B 2018/1861* (2013.01); *A61B 2018/1884* (2013.01)

(58) Field of Classification Search
CPC ..... A61B 18/1815; A61B 18/18; A61B 18/12; A61B 18/04; A61B 18/1206; A61B 2018/0063; A61B 2018/183; A61B 2018/1884; A61B 2018/1823; A61B 2018/00785; A61B 2018/1876; A61B 2018/00577; A61B 2018/00732; A61B 2018/1861; A61B 2018/00702; A61B 2018/00738; A61B 2018/0075; A61B 2018/00779; A61B 2018/128; A61B 2018/00404; A61B 2018/00922; A61B 2018/00589; A61B 2018/1273; A61B 2018/1838; A61B 2018/1853; A61B 2018/1892; A61B 2018/00452; A61B 2018/00458; A61B 2018/00464; A61B 2018/0047; A61B 2090/061
See application file for complete search history.

(56) References Cited

U.S. PATENT DOCUMENTS

| | | | |
|---|---|---|---|
| 6,558,385 B1 | 5/2003 | McClurken et al. | |
| 6,702,810 B2 | 3/2004 | McClurken et al. | |
| 6,953,461 B2 | 10/2005 | McClurken et al. | |
| 7,115,139 B2 | 10/2006 | McClurken et al. | |
| 7,645,277 B2 | 1/2010 | McClurken et al. | |

(Continued)

OTHER PUBLICATIONS

Extended European Search Report from EP Application EP 22157614.3, dated Jul. 6, 2022, 8 pgs.

*Primary Examiner* — Joseph A Stoklosa
*Assistant Examiner* — Marina Delaney Templeton
(74) *Attorney, Agent, or Firm* — Husch Blackwell LLP

(57) ABSTRACT

Devices, kits, and methods described herein are usable for medical treatments by generating local maxima using constructive interference of multiple oscillator outputs. Where constructive interference occurs between the oscillator waves, the output signal can have significant strength to cause heating and coagulation at a bleeding vessel, for instance, while at areas with little interaction (or with destructive interference) there is insufficient power dissipated by the output signal to cause heating sufficient to cause coagulating heating.

19 Claims, 9 Drawing Sheets

(56) References Cited

U.S. PATENT DOCUMENTS

| | | | |
|---|---|---|---|
| 2002/0026188 A1* | 2/2002 | Balbierz | A61B 18/1206 |
| | | | 606/41 |
| 2005/0251233 A1* | 11/2005 | Kanzius | A61N 1/406 |
| | | | 607/101 |
| 2009/0132015 A1* | 5/2009 | Miller | A61B 18/18 |
| | | | 607/101 |
| 2010/0087808 A1* | 4/2010 | Paulus | A61B 18/18 |
| | | | 606/33 |
| 2010/0145328 A1* | 6/2010 | Hancock | A61B 18/1815 |
| | | | 606/33 |
| 2010/0268211 A1 | 10/2010 | Manwaring et al. | |
| 2013/0267943 A1* | 10/2013 | Hancock | H05B 6/806 |
| | | | 606/33 |
| 2015/0082624 A1* | 3/2015 | Craig | A61B 46/10 |
| | | | 606/51 |
| 2015/0282860 A1* | 10/2015 | Anderson | A61B 18/1206 |
| | | | 606/34 |
| 2016/0013855 A1 | 1/2016 | Campos et al. | |
| 2020/0022755 A1* | 1/2020 | Hancock | A61B 18/1815 |
| 2022/0160427 A1* | 5/2022 | McErlean | A61B 18/1815 |
| 2023/0293247 A1* | 9/2023 | Hancock | A61B 18/1206 |
| | | | 700/245 |

* cited by examiner

200

212

318

316

314

312

310

MICROWAVE SEALER DEVICE AND GENERATOR

FIELD

The present technology is generally related to microwave sealing of bleeding vessels in electrosurgery.

BACKGROUND

Rapid sealing of bleeding vessels is useful in a number of procedures, and has applications in various fields such as orthopaedics, spine treatments, oncology, neurosurgery, thoracic surgery, and cardiac implantable electronic devices. Electrosurgery typically uses high-frequency electrical current (e.g., about 200 kHz to about 3.3 MHz), which is above the range that will cause nerve or muscle stimulation.

Existing electrosurgical sealing solutions include the AQUAMANTYS™ bipolar and monopolar sealers that are commercially available from the applicant, Medtronic. The AQUAMANTYS™ sealers use a combination of radiofrequency (RF) energy and saline to provide hemostatic sealing of soft tissue and bone during surgery.

Monopolar sealers operate by routing voltage from an active circuit to a handpiece that includes a single tip. The tip emits signal through the tissue to be treated, and charge is collected at a return pad that completes the circuit through the patient's body. In some procedures the patient can lie upon the return pad during treatment. Treatments can be tailored by changing the frequency or voltage of the active circuit, or by changing the position of the tip, or by use of fluid such as saline as described in the applicant's commonly owned patents U.S. Pat. Nos. 6,558,385, 6,702,810, 6,953,461, 7,115,139, and 7,645,277. Use of saline flow around an RF probe to improve effectiveness of coagulation and tissue sealing is a part of many MEDTRONIC® TRANSCOLLATION® devices and surgical procedures.

Bipolar sealers also deliver electrical signal and, optionally, saline or other fluid, but do so in a different manner. In a bipolar system, rather than a single tip the handpiece includes two tips. Because current can travel between the two tips of the handpiece, no return pad is needed in operation of a bipolar system.

Bipolar and monopolar systems are used in different procedures depending on the objective to be accomplished. A primary consideration is the desired current path. Current in a bipolar system typically follows a shallow path near the tips of the handpiece, whereas current in a monopolar system travels between the tip of the handpiece and the return pad, which is often a longer, deeper current path.

While existing monopolar and bipolar systems are effective for a number of treatments, it would be beneficial to provide a system that permits for targeted depth of treatment that may not be at the shallow depth of typical treatment with a bipolar system. Additionally, the use of conventional systems requires that the handpiece be either sanitized or disposed of after use due to patient contact, and it would be desirable to provide a reusable or easily cleanable alternative to reduce waste or cleaning and sanitization costs.

SUMMARY

The techniques of this disclosure generally relate to a device having two signal generators, operable together to constructively interfere at a desired depth of treatment. In this way, coagulation is provided at a targeted depth, without the need for physical contact between the emitting device and the patient.

In one aspect, a system includes a plurality of oscillators. A processor is configured to drive the oscillators such that at least one of the plurality of processors has a different phase or frequency from another one of the plurality of processors. A combiner is arranged to receive an output from each of the plurality of oscillators to generate a summed output. An amplifier is arranged to receive the summed output and configured to generate a signal. Finally, a directional antenna is configured to output the signal.

In embodiments, the plurality of processors can include two oscillators. In other embodiments, the plurality of processors can include three oscillators. The system can include a plurality of operational buttons. The directional antenna and the plurality of operational buttons can be arranged at a housing. The plurality of oscillators, the combiner, and the amplifier can also be arranged within the housing in some embodiments. A disposable bag can be arranged around the housing. A wire can electronically couple the directional antenna to the amplifier. A sensor can be used to determine a distance between the system and a material comprising a target.

According to another aspect, a method for treating a target includes operating a first oscillator at a first frequency, a first phase, and a first amplitude to generate a first output; operating a second oscillator at a second frequency, a second phase, and a second amplitude to generate a second output; combining and amplifying the first output and the second output to generate a signal; and emitting the signal at a directional antenna. The first frequency can be different from the second frequency, and the first frequency and the second frequency are selected such that the signal has sufficient strength to treat the target due to constructive interference between the first output and the second output.

In embodiments, the first phase is different from the second phase, and additionally or alternatively the first amplitude can be different from the second amplitude. Embodiments can include a third oscillator operated at a third frequency, a third phase, and a third amplitude to generate a third output, and the method can include combining and amplifying the first output, the second output, and the third output to generate the signal.

According to another aspect, a kit includes a device that includes a plurality of oscillators; a processor configured to drive the oscillators such that at least one of the plurality of processors has a different phase or frequency from another one of the plurality of processors; a combiner arranged to receive an output from each of the plurality of oscillators to generate a summed output; an amplifier arranged to receive the summed output and configured to generate a signal; and a directional antenna configured to output the signal. The kit can include a housing configured to contain the directional antenna, the housing further comprising a plurality of buttons, and a disposable package configured to contain the housing.

In embodiments, within the kit the plurality of oscillators, the combiner, and the amplifier are arranged within the housing. The kit can be sterilizable. The kit can include a wire configured to connect the directional antenna and the amplifier. The kit can include a battery. The kit can also include a sensor configured to determine a distance between the directional antenna and a material comprising a target.

The details of one or more aspects of the disclosure are set forth in the accompanying drawings and the description below. Other features, objects, and advantages of the techniques described in this disclosure will be apparent from the description and drawings, and from the claims.

Figure 1:
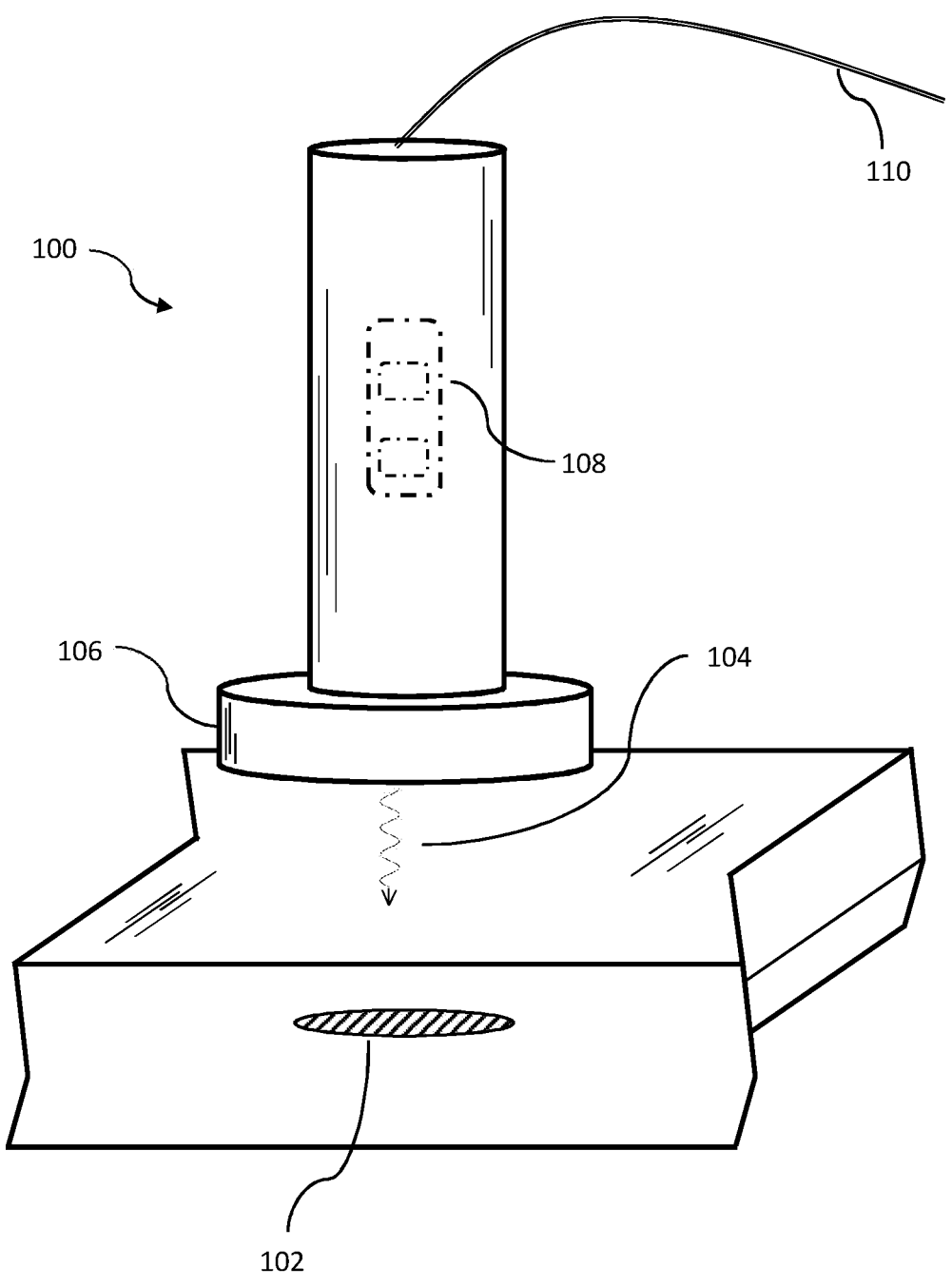
FIG. 1 is a perspective view of a system for providing depth-targeted treatment according to an embodiment.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

As described herein, use of multiple electromagnetic signal generators having different frequencies provides a depth-targeted signal that can be used for coagulation or other treatments that are more precisely positioned than is possible with either conventional monopolar or bipolar systems. Embodiments described herein use two or more signal generators and combine their outputs to take advantage of constructive and destructive interference patterns to provide treatment at a distance from the handle.

FIG. 1 depicts a system according to a first embodiment. As shown in FIG. 1, a handheld device 100 is used to treat a target 102 that can be, for example, a blood vessel that is to be coagulated by heat treatment.

In operation, handheld device 100 emits a signal 104 directed towards the target 102, such as from an antenna housed in a distal end 106 of the handheld device 100. Optionally, handheld device 100 can include controls 108. These controls 108 can be used, in embodiments, to set the depth of treatment or turn the signal 104 on or off. For devices to be used in a surgical setting, controls 108 can be buttons or other similar features that are manipulatable while wearing gloves. The handpiece can include activation buttons and a highly directional antenna or electromagnetic concentrator, and optionally a microwave power sense circuit as described in more detail below.

Wire 110 optionally connects the device 100 to other components that can include a power source, remote controlling software or computing resources, or recording equipment that collects data on treatment, for example. Device 100 can be disposable, in embodiments. This can be beneficial in a surgical environment where reusing devices requires sterilization and repackaging. By using wire 110, expensive components such as batteries and processors can be moved out of the handheld device 100 and those resources can be housed in a remote location such as an electrosurgical unit (ESU) (not shown).

In some embodiments, a battery can be included within the device 100. In such embodiments, and particularly if the oscillators, combiner, processor, and amplifier are loaded into the handheld device's housing, there may not be a need for any wire 110, as there is no need for data or power transmission. Providing a battery in the handheld device makes the device easier to operate by removing potentially entangling structures and facilitating complete bagging of the handheld device. In embodiments, the battery can be removed and replaced, or the battery can be recharged. In some embodiments, wire 110 can be plugged in or removed from the handheld device 100 to charge the battery, or to facilitate data transmission. In still other embodiments, data, power transmission, or both to the device 100 can be accomplished wirelessly.

As will be described in more detail below, device 100 provides a radio frequency signal that is a combination of at least two oscillating signals. When two sinusoidal signals having different phases or frequencies are combined, "beat" frequencies can be generated in which the two signals alternatively constructively or destructively interfere. When there is constructive interference the total output signal is high, and when there is destructive interference the total output signal is low. Taking advantage of the constructive and destructive interference patterns generated in this way, it has been found that surgical targets at a depth can be targeted by device 100.

This is a significant improvement for some treatments that have conventionally been addressed by use of either a monopolar or bipolar device. As an initial matter, treatment can be provided in a standoff arrangement as shown in FIG. 1, in which the device is not required to be in contact with the patient. This can be beneficial for purposes of cleaning or sterilization. In some treatments, treatment at a depth makes the process less invasive, and can prevent cutting the patient to get to the target 102.

Figure 2:
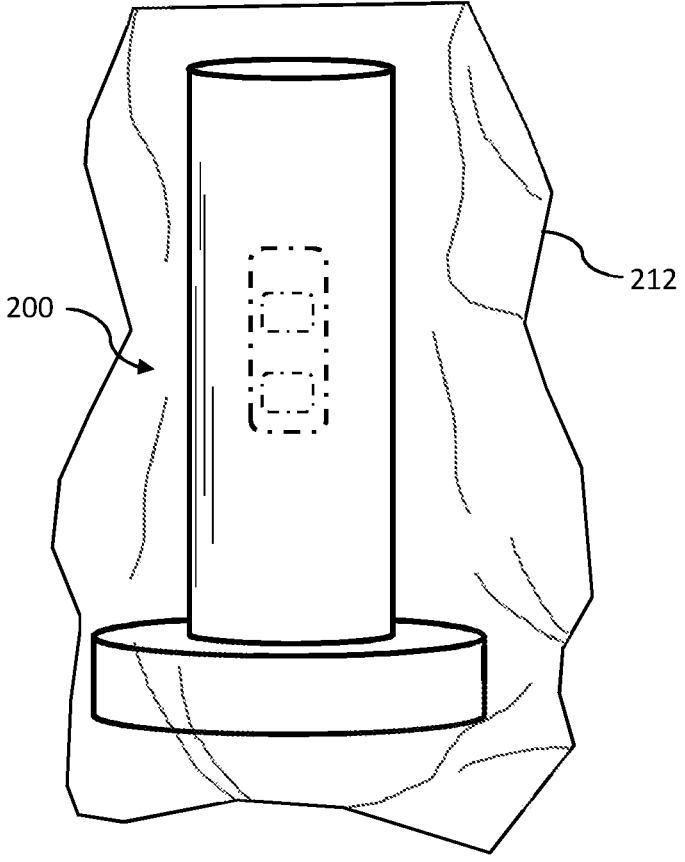
FIG. 2 is an alternate view of the device used in the system of FIG. 1 arranged in a disposable container.

FIG. 2 shows an alternative version—device 200—that is housed within a disposable bag 212. As described with respect to FIG. 1, treatment that is provided at a depth does not require direct contact between the device 200 and a target (not shown, see target 102 of FIG. 1) to be treated. Disposable bag 212 can be a clear plastic bag, for example, that prevents device 200 from being contaminated during a treatment. After the treatment is concluded, disposable bag 212 can be removed and replaced prior to reuse of the device 200.

Figure 3A:
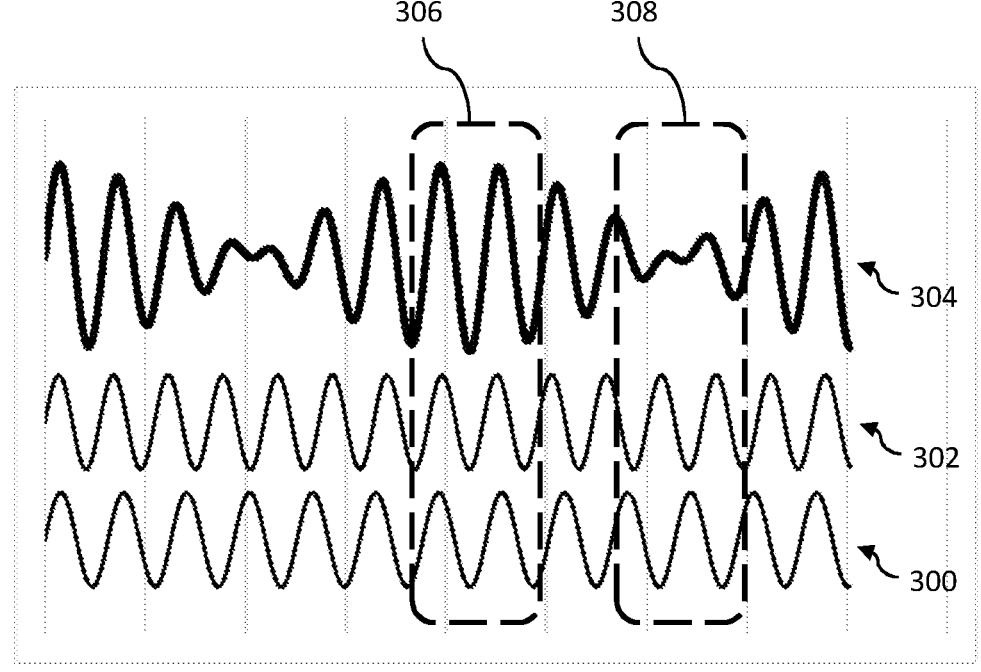
FIGS. 3A and 3B are charts of constructively and destructively interfering signal from multiple sources.

FIG. 3A depicts the "beat" pattern of two combined sinusoidal waves as mentioned above with respect to FIG. 1. Specifically, FIG. 3A shows two waves, 300 and 302, that have different frequencies. Combined wave 304 is the sum of first wave 302 and second wave 304. Each of the waves 300, 302, and 304 are arranged along a common abscissa and separated along the ordinate in FIG. 3A for ease of understanding.

FIG. 3A shows two regions, 306 and 308, corresponding to constructive and destructive interfering regions, respectively. In a treatment system, constructive interference at region 306 may be sufficient to cause heating and coagulation, whereas destructive interference region 308 (and indeed all other regions at which the amplitude of the combined wave 304 is below a threshold) corresponds to regions where no treatment will occur. By selectively creating a constructive interference region 306 at a treatment site such as target 102 of FIG. 1, treatment can be performed at a distance from the RF antenna or source.

Figure 3B:
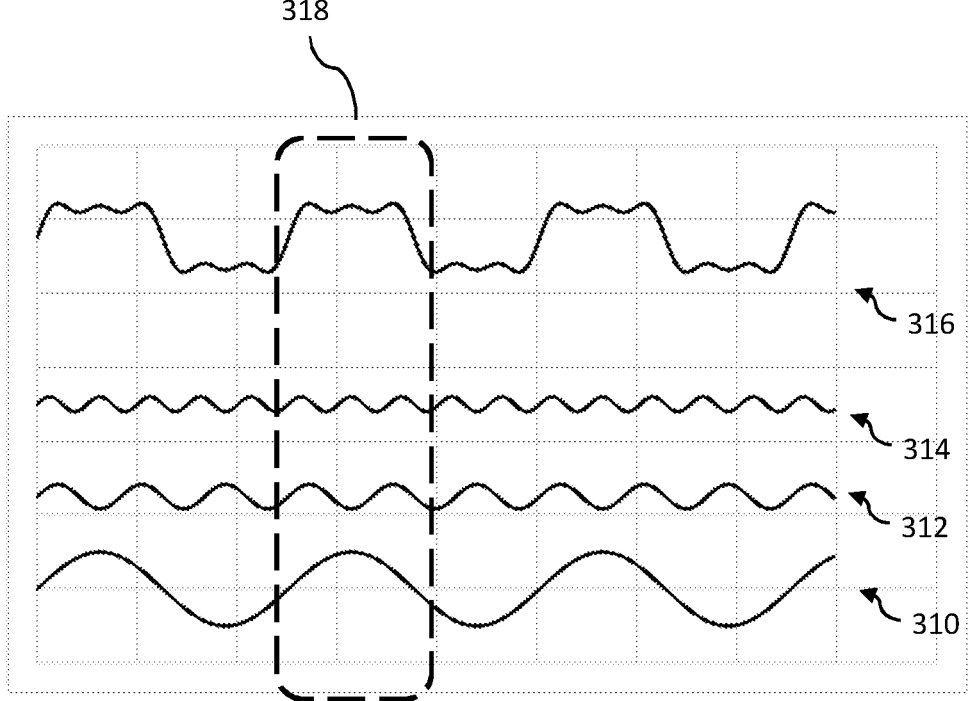

FIG. 3B shows constructive and destructive interference of three waves rather than two. FIGS. 3A and 3B are for illustrative purposes only, and it should be understood that in embodiments there could be any number of oscillators each producing signals having different characteristics from the others to create desired constructive and destructive interference patterns.

In FIG. 3B, first wave 310, second wave 312, and third wave 314 are all sinusoidal. Each has a different amplitude, phase, and frequency. Their sum, wave 316, can therefore be more complex than the combined wave 304 of FIG. 3A. In FIG. 3B, the first wave 310, second wave 312, and third wave 314 are selected as the first three harmonics in the Fourier series for a square wave, for example, though in practice the frequencies, phase shifts, and amplitudes of each wave 310, 312, and 314 can be targeted to create a constructively interfering region 318 at any desired depth.

Figure 4A:
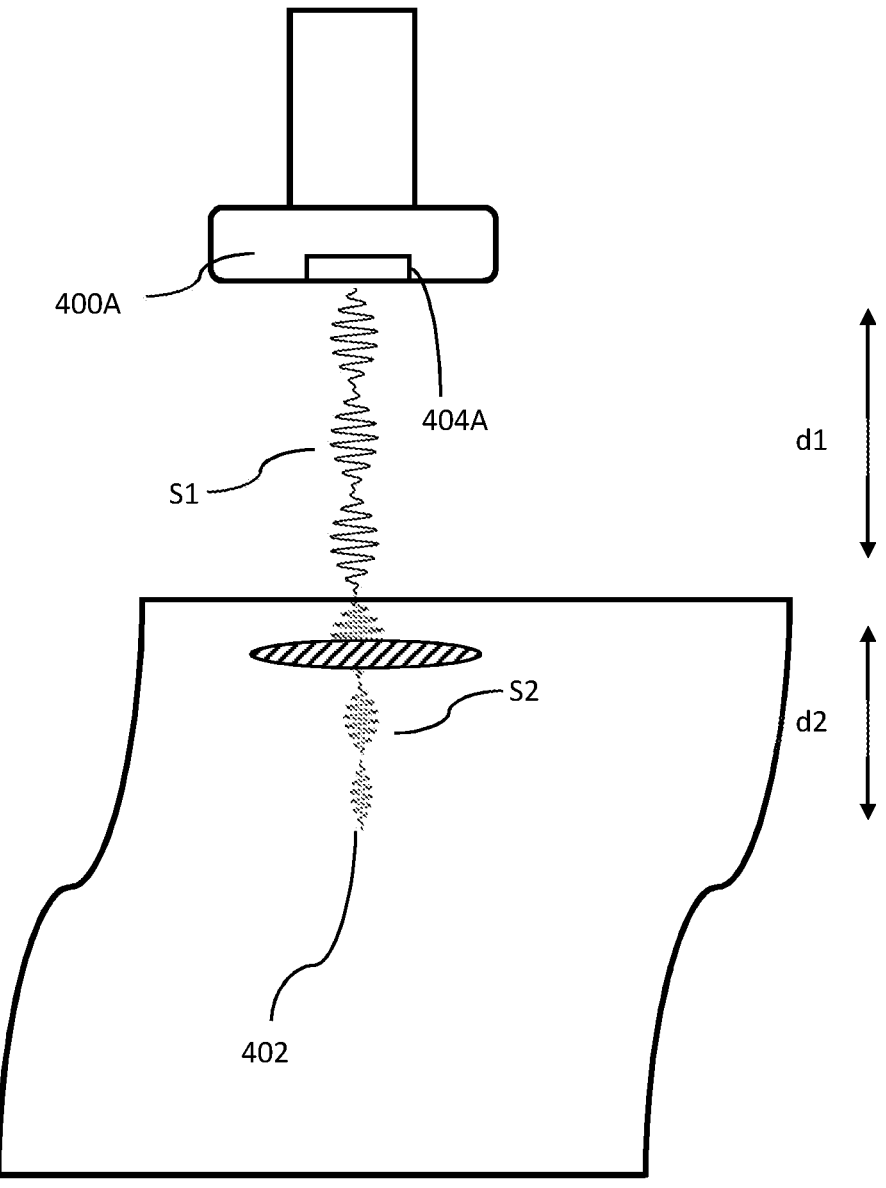
FIG. 4A is a schematic depiction of operation of a system providing depth-targeted treatment according to a first embodiment that operates in a standoff condition.

FIG. 4A shows a simplified schematic of a signal pathway from a device 400A according to an embodiment towards a target 402. As shown in FIG. 4A, device 400A stands off from the target 402 by a distance made up of two parts: a first distance d1 through the air (or other ambient environment), and a second distance d2 through the body of the patient.

Due to the difference in index of refraction between the environment and the patient's body, the signal has a first portion S1 and a second portion S2, and the wavelength of the signal in second portion S2 is higher than in the first portion S1. In embodiments, the antenna 404A of the device 400A can account for the path length as well as the portion of that path length that is within each material having a different index of refraction. While FIG. 4A is designed to show multiple peaks, it should be understood that at least within the body (i.e., in second distance d2) the first peak is preferably at the target treatment site. The signal will also attenuate over distance, especially when the constructive peaks of the signal occur in a material is one in which electromagnetic signals will decay.

Figure 4B:
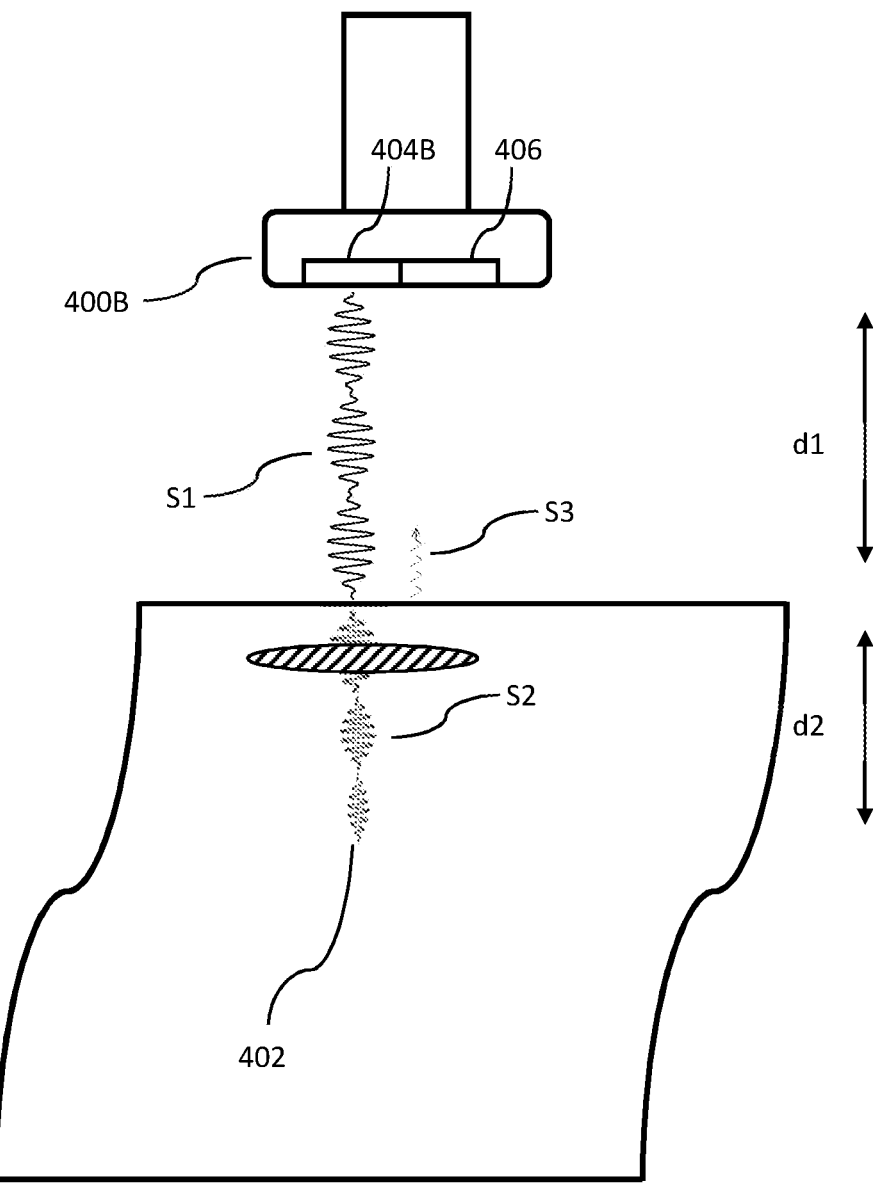
FIG. 4B is a schematic depiction of operation of a system providing depth-targeted treatment according to a second embodiment that includes a feedback sensor.

FIG. 4B shows an embodiment of a device 400B that is similar to the device 400A, except that it includes a sensor 406. As shown in FIG. 4B, at each interface between two materials having different indices of refraction there is at least some portion of the signal S1 that is transmitted S2, but another portion that is reflected S3. The reflected signal S3 can be detected by sensor 406 to determine the distance D1 and accurately set the frequencies, amplitudes, and phases of the oscillators within the device 400B (not shown) to ensure constructive interference occurs at the target 402. The distance can, in embodiments, be determined by use of a visible laser light that can identify the target point.

It should be understood that sensor 406 need not rely on the reflected wave S3 to determine distance S3, and could instead sense the distance d1 using any of a variety of distance measuring techniques that will be apparent to those of skill in the field of optical systems design, such as by emitting and detecting a reflected infrared, ultrasonic, or visual-region optical beam.

Figure 4C:
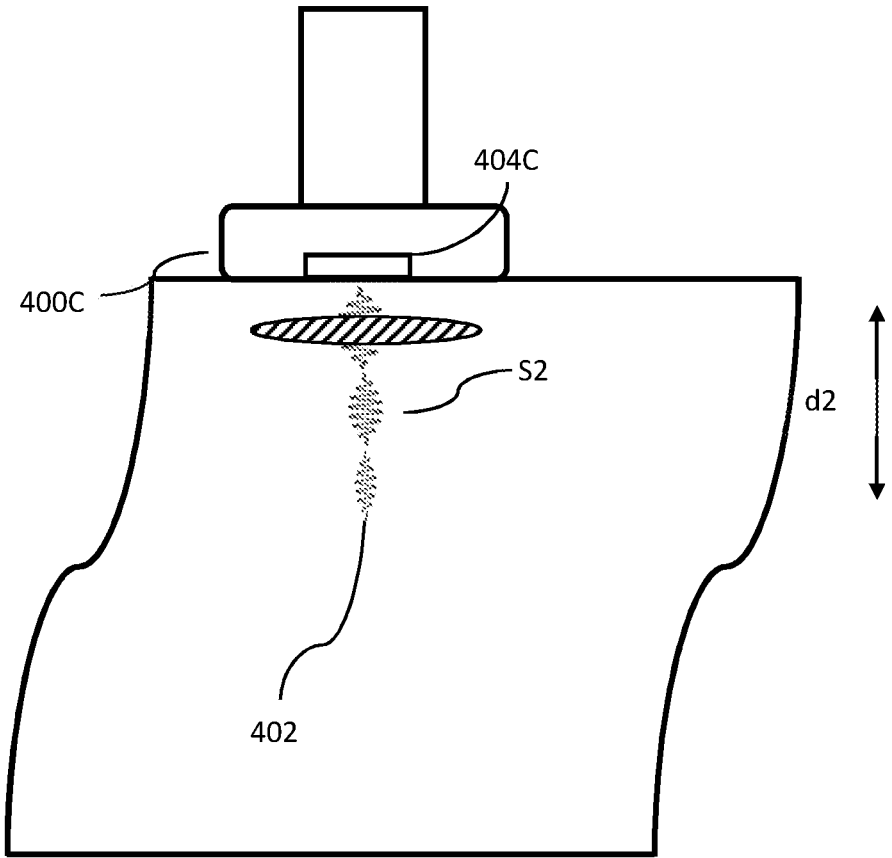
FIG. 4C is a schematic depiction of operation of a system providing depth-targeted treatment according to a third embodiment that operates in direct contact with a tissue to be treated.

FIG. 4C shows a third embodiment of a device 400C that is similar to the devices 400A and 400B, except that it operates in contact with (or nearly in contact with) the patient. In this case, d1 (FIGS. 4A, 4B) is effectively zero.

Figure 5:
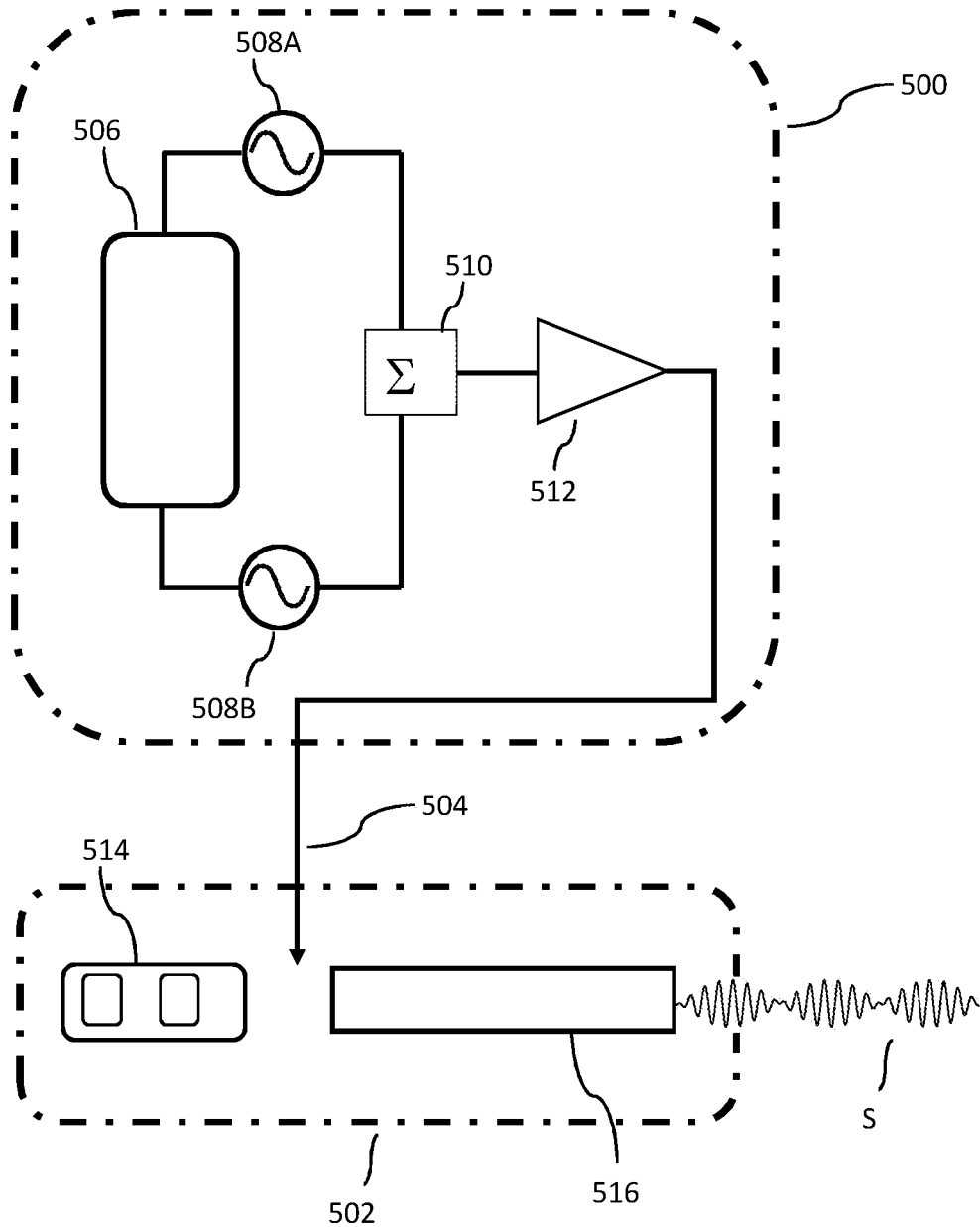
FIG. 5 depicts a circuit configured to provide a depth-targeted treatment signal according to an embodiment.

FIG. 5 is a design of a device or system as described above. As shown in FIG. 5, an electrosurgical unit (ESU) 500 is connected to a handheld device 502 via a conductor

504. It should be understood that, as described above, in some embodiments the ESU 500 and the handheld device 502 can be physically separated by a cable or wire (i.e., conductor 504) whereas in other embodiments the conductor 504 is an internal component that connects the ESU 500 and the handheld device 502 within a single housing.

Within the ESU 500, a processor 506 is configured to operate two oscillators 508A and 508B. As described above, in various embodiments there could be two, three, or many oscillators. The output of the oscillators 508A, 508B, . . . 508*n* are combined at combiner 510 and amplified at amplifier 512. These components can, in some embodiments, be combined into a single operational amplifier.

In the embodiment shown in FIG. 5 having two oscillators 508A and 508B, the voltages are expected to be:

At output of 508A: $\sin(2\pi f_1 t + \theta_1)$

At output of 508B: $\sin(2\pi f_2 t + \theta_2)$ where $f_1$ and $f_2$ affect frequency, and $\theta_1$ and $\theta_2$ affect phase offset of 508A and 508B, respectively. From these two equations, it can be expected that the combined voltage output from ESU 500 is:

$$\sin(2\pi f_1 t + \theta_1) + \sin(2\pi f_2 t + \theta_2)$$

The maxima and minima can be found where this expression is equal to $\{2 \text{ or } -2\}$ or $\{0\}$, respectively. For the maxima, at which constructive interference is occurring, this means $$2\pi f_1 t + \theta_1 = 2\pi f_2 t + \theta_2$$

and for the minima, at which destructive interference is occurring, this means $$2\pi f_1 t + \theta_1 = 2\pi f_2 t + \theta_2 + \pi$$

By adjusting $f_1$, $f_2$, $\theta_1$, and $\theta_2$, the time t can be adjusted for either maximum or minimum amplitude. Time t to reach the target can be estimated based on the distance to that target, as well as the refractive indices of the various portions of the path to arrive at that target, which can be determined as described above with respect to FIGS. 4A-4C.

The equations above follow the simple case where amplitudes between the oscillators 508A and 508B are equivalent, and where there are only two oscillators. It should be understood both the number of oscillators and the amplitude of each oscillator can be modified in other embodiments to create a desired wave profile.

As shown in FIG. 5, switches 514 are positioned on the handheld device 502. These switches are illustrative only, and in embodiments could be either a simple on-off (as shown) or could be more complex, such as including a depth-setting gauge or a display that indicates distance to a target, distance to the patient, operational state (on, off, error, or power level, for example).

Handheld device also includes highly-directional antenna 516. Directional antenna 516 can provide concentrated and highly-directional, narrowly focused energy towards the target, such as a bleeding vessel.

In sum, the devices and systems described herein provide microwave signal to seal bleeding vessels or provide other similar therapies. The outputs of two or more software-controlled microwave controllers with various phase, frequency, and/or amplitude can be combined to create a standing wave at different positions in the transmission path. Accordingly, the resultant microwave signal can be targeted to reach a power suitable to increase a target tissue's temperature based on the location where constructive interference between the two outputs occurs. The frequency and phase of the oscillators can be adjusted to achieve the desired depth of effect, and the gain of an amplifier can be adjusted to achieve the desired intensity of the effect. Power can be in the range of a few hundred watts and frequency could be in the range of 2-3 GHz that could create about 10 cm depth of effect, for example.

Figure 6:
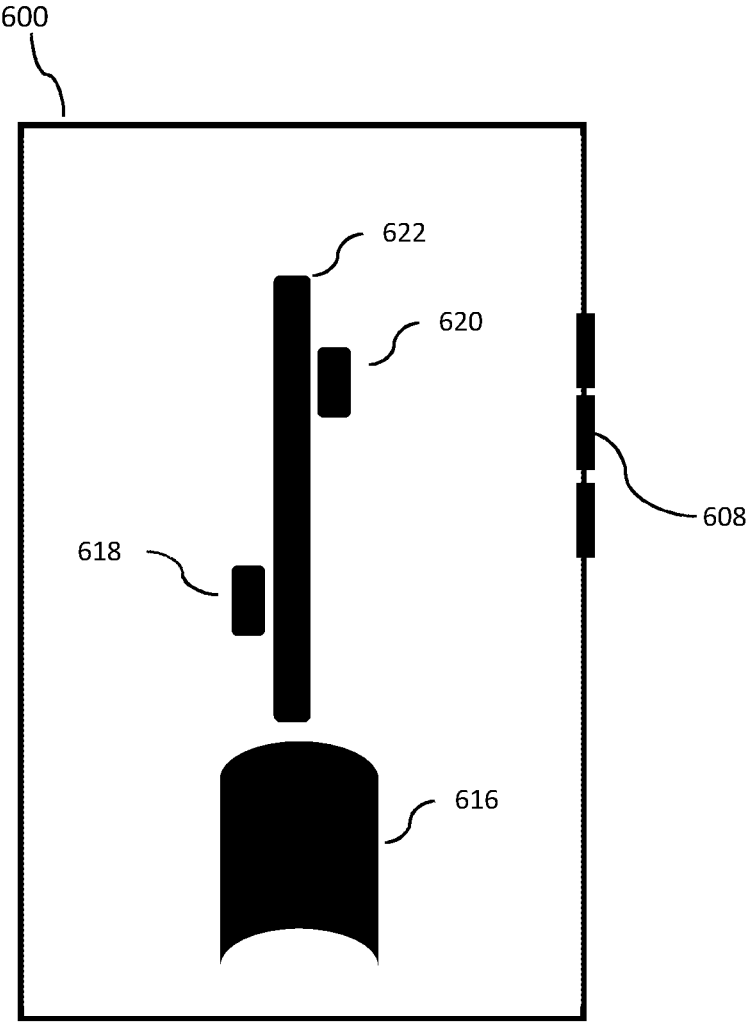
FIG. 6 is a schematic view of a device having both rear- and front-sensing circuits, according to an embodiment.

FIG. 6 shows a device 600 that includes buttons 608 on the housing thereof. Internally, device 600 includes an antenna 616 (similar to antenna 516 of FIG. 5). Additionally, FIG. 6 shows a forward-sense circuit 618 and a reverse-sense circuit 620 coupled to a transmission line 622. The sensed forward power detected by forward-sense circuit 618 can be used to define the relative depth of treatment effect from the device 600. The sensed reversed power detected by rear-sense circuit 620 can be used to define what is in front of the antenna (e.g., distance from tissue).

The enclosure or housing of the device 600 is made from non-electromagnetically sensitive material in front of the antenna to act as a radome to protect the antenna from surgical field while allowing the EM signal to pass through. Transmission line 622 can be coupled to another device, such as an ESU, via a cable as previously described. Alternatively, the circuitry and/or power supply that drive the antenna 616 can be arranged in the device 600 directly, in embodiments.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A system comprising:

a plurality of oscillators;

a processor configured to drive the plurality of oscillators such that at least one of the plurality of oscillators has a different phase or frequency from another one of the plurality of oscillators;

a combiner arranged to receive an output from each of the plurality of oscillators and configured to, based on the received output, generate a summed output, wherein the summed output includes at least a first microwave signal and a second microwave signal such that the first microwave signal and second microwave signal alternatingly constructively and destructively interfere;

an amplifier arranged to receive the summed output and configured to, based on the summed output, generate a signal;

a directional antenna configured to output the signal at a depth within a user that seals a targeted tissue area in a standoff arrangement relative to the user, such that no contact between the device and the user or no incisions to the user is required, wherein the directional antenna is contained within a housing and behind a non-electromagnetically sensitive material;

a forward-sense circuit configured to sense forward power from the system to define the depth within the user of treatment effect from the system; and a reverse-sense circuit configured to sense reversed power back to the system to define a distance from tissue of the user.

2. The system of claim 1, wherein the plurality of oscillators consists of two oscillators.

3. The system of claim 1, wherein the plurality of oscillators consists of three oscillators.

4. The system of claim 1, further comprising a plurality of operational buttons.

5. The system of claim 4, wherein the plurality of operational buttons are arranged on the housing.

6. The system of claim 5, wherein the plurality of oscillators, the combiner, and the amplifier are arranged within the housing.

7. The system of claim 6, further comprising a disposable bag arranged around the housing.

8. The system of claim 5, further comprising a disposable bag arranged around the housing.

9. The system of claim 5, further comprising a wire that electronically couples the directional antenna to the amplifier.

10. A method for treating a target, the method comprising:

operating a first oscillator at a first frequency, a first phase, and a first amplitude to generate a first microwave signal output;

operating a second oscillator at a second frequency, a second phase, and a second amplitude to generate a second microwave signal output;

combining and amplifying the first microwave signal output and the second microwave signal output to generate a signal;

emitting the signal at a directional antenna, the directional antenna contained within a housing and behind a non-electromagnetically sensitive material;

sensing forward power with a forward-sense circuit to define the depth within the user of treatment effect; and sensing reversed power with a reverse-sense circuit to define a distance from tissue of the user, wherein the first frequency is different from the second frequency, and the first frequency and the second frequency are selected such that the signal has sufficient strength to seal the target at a depth within a user in a standoff arrangement relative to the user due to constructive interference between the first microwave signal output and the second microwave signal output, such that no contact with the user or no incisions to the user is required.

11. The method of claim 10, wherein the first phase is different from the second phase.

12. The method of claim 10, wherein the first amplitude is different from the second amplitude.

13. The method of claim 10, further comprising operating a third oscillator at a third frequency, a third phase, and a third amplitude to generate a third output, and combining and amplifying the first output, the second output, and the third output to generate the signal.

14. A kit comprising:

a device including:

plurality of oscillators;

a processor configured to drive the oscillators such that at least one of the plurality of oscillators has a different phase or frequency from another one of the plurality of oscillators;

a combiner arranged to receive an output from each of the plurality of oscillators to generate a summed output, wherein the summed output includes at least a first microwave signal and a second microwave signal such that the first microwave signal and second microwave signal alternatingly constructively and destructively interfere;

an amplifier arranged to receive the summed output and configured to generate a signal;

a directional antenna configured to output the signal at a depth within a user that seals a targeted tissue area in a standoff arrangement relative to the user, such that no contact between the device and the user or no incisions to the user is required;

a forward-sense circuit configured to sense forward power from the system to define the depth within the user of treatment effect from the system; and a reverse-sense circuit configured to sense reversed power back to the system to define a distance from tissue of the user, a housing configured to contain the directional antenna behind a non-electromagnetically sensitive material, the housing further comprising a plurality of buttons;

a disposable package configured to contain the housing.

15. The kit of claim 14, wherein the plurality of oscillators, the combiner, and the amplifier are arranged within the housing.

16. The kit of claim 15, further comprising a wire configured to connect the directional antenna and the amplifier.

17. The kit of claim 15, further comprising a battery.

18. The kit of claim 14, wherein the kit is sterilizable.

19. The kit of claim 14, further comprising a sensor configured to determine a distance between the directional antenna and a material comprising a target.

* * * * *